(12) United States Patent
Lee (10) Patent No.: US 11,285,236 B2
(45) Date of Patent: Mar. 29, 2022

(54) AROMATHERAPY DEVICE

(71) Applicant: PUZHEN LIFE CO., LTD., Shatin (HK)

(72) Inventor: Andy Lee, Shatin (HK)

(73) Assignee: Puzhen Life Co., Ltd., Shatin (HK)

( * ) Notice: Subject to any disclaimer, the term of this patent is extended or adjusted under 35 U.S.C. 154(b) by 110 days.

(21) Appl. No.: 16/810,625

(22) Filed: Mar. 5, 2020

(65) Prior Publication Data

US 2021/0178006 A1 Jun. 17, 2021

(30) Foreign Application Priority Data

Dec. 17, 2019 (CN) .......................... 201922279653.9

(51) Int. Cl.
*A61L 9/14* (2006.01)
*A61L 9/12* (2006.01)

(52) U.S. Cl.
CPC ................. *A61L 9/14* (2013.01); *A61L 9/122* (2013.01); *A61L 2209/134* (2013.01)

(58) Field of Classification Search
None
See application file for complete search history.

(56) References Cited

U.S. PATENT DOCUMENTS

2015/0137395 A1* 5/2015 Wolf .................... B60H 3/0007
261/121.1

FOREIGN PATENT DOCUMENTS

WO WO-9314172 A1 * 7/1993 ......... A61K 48/0008

* cited by examiner

*Primary Examiner* — Jelitza M Perez
(74) *Attorney, Agent, or Firm* — Robert L. Stearns; Dickinson Wright, PLLC (57) ABSTRACT

An aromatherapy device comprises a housing and an atomizing device configured for atomizing essential oil to be sprayed out, the housing is provided with a receiving chamber configured for fittingly receiving the atomizing device, and the receiving chamber is provided therein with an pop-up mechanism configured for launching the atomizing device out. The aromatherapy device provided in the present application is provided with a receiving chamber in the housing, and the receiving chamber is used to receive the atomizing device, such that the atomizing device can be quickly hidden inside the receiving chamber when used, and the atomizing device can be detachably connected to the housing to prevent the atomizing device from being damaged by touching.

17 Claims, 10 Drawing Sheets

//AROMATHERAPY DEVICE

CROSS REFERENCE TO RELATED APPLICATION

The present application claims priority to Chinese Patent Application Ser. No. CN201922279653.9, filed on Dec. 17, 2019, the entire content of which is incorporated herein by reference.

TECHNICAL FIELD

The present application relates to the technical field of air purifying, and more particularly to an aromatherapy device.

BACKGROUND

With the continuous improvement of people's living standards, more and more people have started to use aromatherapy machines to atomize the essential oils to be dispersed mist-like particles into the air, to improve the air quality of the indoor environment, which has the effect of curing diseases and attaining mental tranquility, as well as health care and physical therapy. It has excellent auxiliary effects on skin allergies, insomnia, colds, cough and asthma. The atomizing device of the current aromatherapy machine is generally fixedly connected to a base housing, when the atomizing device is damaged, the atomizing device is not convenient to be repaired and replaced, and the use cost is high.

SUMMARY

An object of the present application is to provide an aromatherapy device, in order to solve the problem existed in relative technology that an atomizing device of an aromatherapy device is not convenient to be repaired and replaced.

In order to solve above mentioned object, the present application adopts the technical solution is providing an aromatherapy device, including:

a housing; and an atomizing device, configured for atomizing essential oil to be sprayed out;

wherein the housing is provided with a receiving chamber configured for fittingly receiving the atomizing device, and the receiving chamber is provided therein with an pop-up mechanism configured for launching the atomizing device out.

In an embodiment, the pop-up mechanism includes:

an outer sleeve, fixed in the receiving chamber;

an inner sleeve, configured for receiving the atomizing device;

a spring, configured to elastically push the inner sleeve, outwardly; and a locking structure, configured to lock the inner sleeve into the outer sleeve;

the inner sleeve is slidably mounted in the outer sleeve, the spring is placed in the outer sleeve, the locking structure is connected with the outer sleeve, and the inner sleeve is connected with the atomizing device.

In an embodiment, an inner sidewall of the outer sleeve is concaved to form a sliding groove, and an outer sidewall of the inner sleeve is protruded with a sliding block configured to be matched with the sliding groove.

In an embodiment, the locking structure comprises a pull rod disposed in the sliding groove and a hook bending from an end of the pull rod toward the sliding block, the other end of the pull rod is fixed at the outer sleeve, and the sliding block is provided with a locking groove configured for enabling the hook to be locked when placed in or unlocked when separated.

In an embodiment, the sliding block is provided with a limiting groove configured for guiding the hook to be moved into the locking groove or separated from the locking groove, and the locking groove is located in the limiting groove.

In an embodiment, the limiting groove is provided with a limiting elastic arm configured for fittingly stopping the hook to limit a moving path of the hook in the limiting groove.

In an embodiment, an inner sidewall of the limiting groove is protruded with a limiting block configured for stopping the hook to limit a moving path of the hook, and a position of the limiting block is corresponding to an opening position of the locking groove.

In an embodiment, the sliding block is provided with a hole configured for a top end of the spring to be placed into, and the hole extends along an axis direction of the inner sleeve, and a bottom end of the spring is connected with an inner bottom surface of the outer sleeve.

In an embodiment, the atomizing device includes:

an essential oil bottle, configured to store essential oils;

an air pump, configured to provide air flow;

an atomizing cover, provided with an atomizing cavity;

an air spraying nozzle, placed in the atomizing cavity;

an air pipe, configured for connecting the air pump and the air spraying nozzle;

an oil suction pipe, extending into of the essential oil bottle; and an oil spraying nozzle, connected with the oil suction pipe;

the atomizing cover is provided with a connecting port configured for fittingly connecting the essential oil bottle, the connecting port is in communication with the atomizing cavity, a position of an air outlet of the air spraying nozzle is located at a position corresponding to an oil outlet of the oil spraying nozzle, the atomizing cover is provided with a mist outlet in communication with the atomizing cavity, and the atomizing cavity is in communication with the mist outlet.

In an embodiment, the housing is provided with an air purification chamber, the aromatherapy device further comprises a fan and a filter net configured to filter and purify the air, the filter net is placed in the air purification chamber, the housing is provided thereon with an air inlet and an air outlet respectively in communication with the air purification chamber, and the filter net is disposed at the air inlet.

One or more technical solutions in the embodiments of the present application have at least one of the following technical effects:

The beneficial effect of the aromatherapy device provided in the present application is that, compared with the prior art, the aromatherapy device provided in the present application is provided with a receiving chamber in the housing, and the receiving chamber is used to receive the atomizing device, such that the atomizing device can be quickly hidden inside the receiving chamber when used, and the atomizing device can be detachably connected to the housing to prevent the atomizing device from being damaged by touching. In addition, the pop-up mechanism for launching the atomizing device out is provided in the receiving chamber, such that when the atomizing device is damaged, the atomizing device can be ejected from the receiving chamber by the pop-up mechanism, and the atomizing device can be easily taken out from the receiving chamber for easy maintenance and replacement of the atomizing device.

BRIEF DESCRIPTION OF THE DRAWINGS

In order to explain the embodiments of the present application more clearly, a brief introduction regarding the accompanying drawings that need to be used for describing the embodiments of the present application or the prior art is given below; it is obvious that the accompanying drawings described as follows are only some embodiments of the present application, for those skilled in the art, other drawings can also be obtained according to the current drawings on the premise of paying no creative labor.

In the drawings, the main numeral referring to the technical features are listing:

1—housing; 11—receiving chamber; 12—air purification chamber; 13—air inlet; 14—air outlet;

2—atomizing device; 21—essential oil bottle; 22—air pump; 23—atomizing cover; 231—atomizing cavity; 232—connecting port; 233—mist outlet; 24—air spraying nozzle; 25—oil spraying nozzle;

3—pop-up mechanism; 31—outer sleeve; 311—sliding groove; 32—inner sleeve; 321—sliding block; 322—locking groove; 323—limiting groove; 324—hole; 33—spring; 34—locking structure; 341—pull rod; 342—hook; 35—limiting elastic arm; 36—limiting block;

4—filter net; 5—fan.

DETAILED DESCRIPTION

In order to make the purpose, the technical solution and the advantages of the present application be clearer and more understandable, the present application will be further described in detail below with reference to accompanying figures and embodiments. It should be understood that the specific embodiments described herein are merely intended to illustrate but not to limit the present application.

It is noted that when a component is referred to as being "fixed to" or "disposed on" another component, it can be directly or indirectly on another component. When a component is referred to as being "connected to" another component, it can be directly or indirectly connected to another component.

It needs to be understood that, terms "the first" and "the second" are only used in describe purposes, and should not be considered as indicating or implying any relative importance, or impliedly indicating the number of indicated technical features. As such, technical feature(s) restricted by "the first" or "the second" can explicitly or impliedly comprise one or more such technical feature(s). In the description of the present application, "a plurality of" means two or more, unless there is additional explicit and specific limitation.

In the description of the present application, it should be noted that the terms "installation", "connecting", and "connected" should be understood in a broad sense, unless explicitly stated and limited otherwise. For example, they may be fixed connections or removable, or integrated; it can be mechanically connected or electrically connected; it can be directly connected or indirectly connected through an intermediate medium; it can be the internal connection of two elements or the interaction between two elements. For those of ordinary skill in the art, the specific meanings of the above terms in the present application can be understood according to specific situations.

Figure 1:
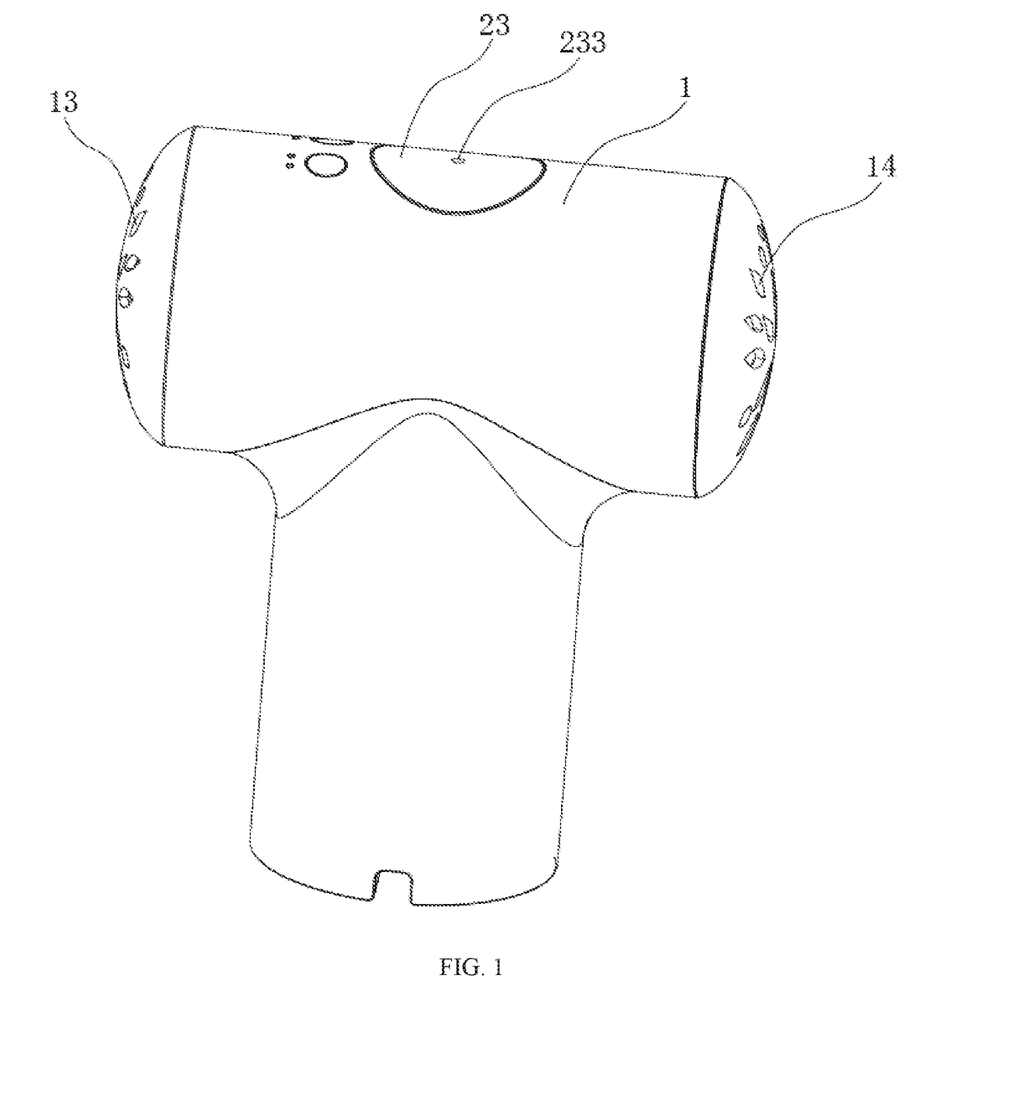
FIG. 1 is a schematic view of perspective structure of an aromatherapy device provided by an embodiment of the present application.

Please refer to FIG. 1, FIG. 2 and FIG. 3 together, and the aromatherapy device provided in the present application will be described below. The aromatherapy device provided in the present application includes a housing 1 and an atomizing device 2 for atomizing essential oils for spraying. The housing 1 is provided with a receiving chamber 11 for fittingly receiving the atomizing device 2. The receiving chamber 11 is provided therein with an pop-up mechanism 3 configured to eject the atomizing device 2 out.

Compared with the prior art, the aromatherapy device provided in the present application is provided with a receiving chamber 11 in the housing 1, and the receiving chamber 11 is used to receive the atomizing device 2, such that the atomizing device 2 can be quickly hidden inside the receiving chamber 11 when used, and the atomizing device 2 can be detachably connected to the housing 1 to prevent the atomizing device 2 from being damaged by touching. In addition, the pop-up mechanism 3 for launching the atomizing device 2 out is provided in the receiving chamber 11, such that when the atomizing device 2 is damaged, the atomizing device 2 can be ejected from the receiving chamber 11 by the pop-up mechanism 3, and the atomizing device 2 can be easily taken out from the receiving chamber 11 for easy maintenance and replacement of the atomizing device 2, the using life of the aromatherapy device can be lengthened, and the using cost of the aromatherapy device can be reduced. In addition, the atomizing device 2 can be quickly removed from the housing 1, which is facilitating the cleaning of the atomizing device 2, in order to facilitate adding or replacing essential oils into the atomizing device 2.

Specifically, the filter net 4 may include, but is not limited to, an electrostatic electret filter net with low wind resistance, high efficiency, and high dust capacity, an activated carbon filter net with a developed void structure and a large surface area, or an efficient particulate air filter (HEPA filter).

Figure 2:
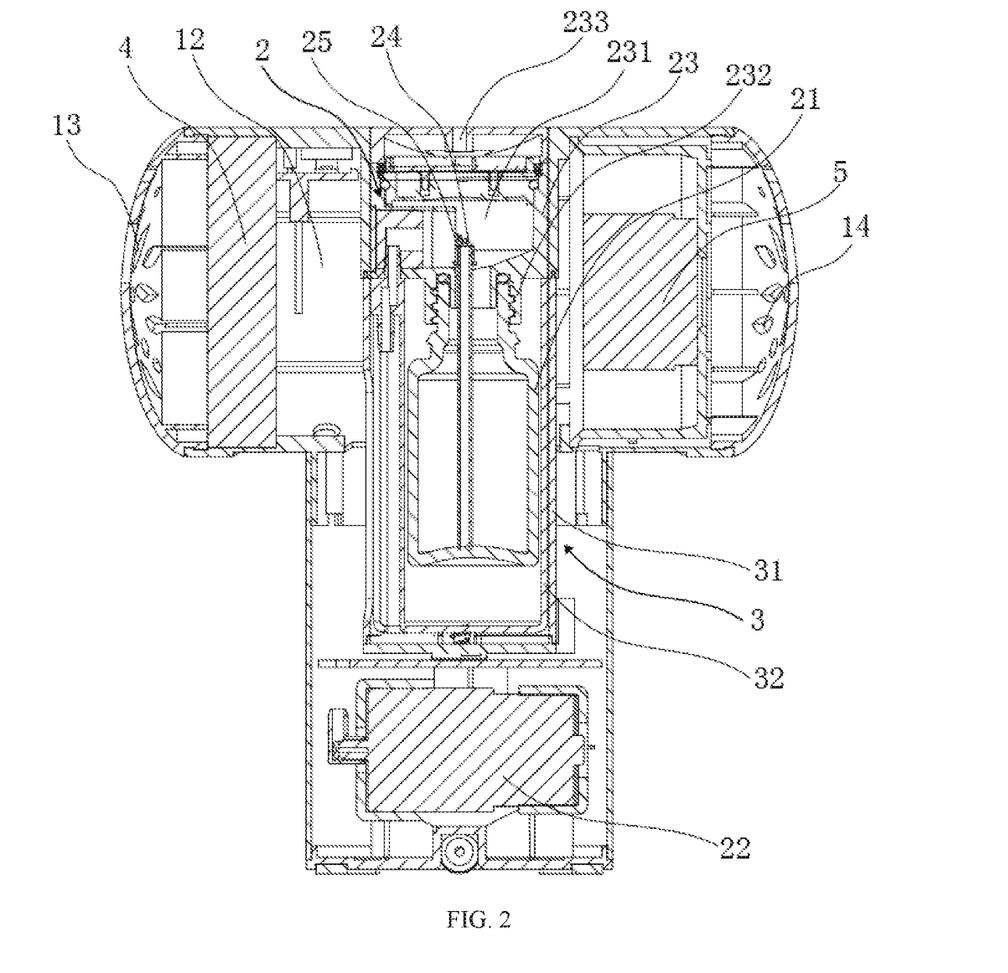
FIG. 2 is a schematic view of a section structure of FIG. 1.
Figure 3:
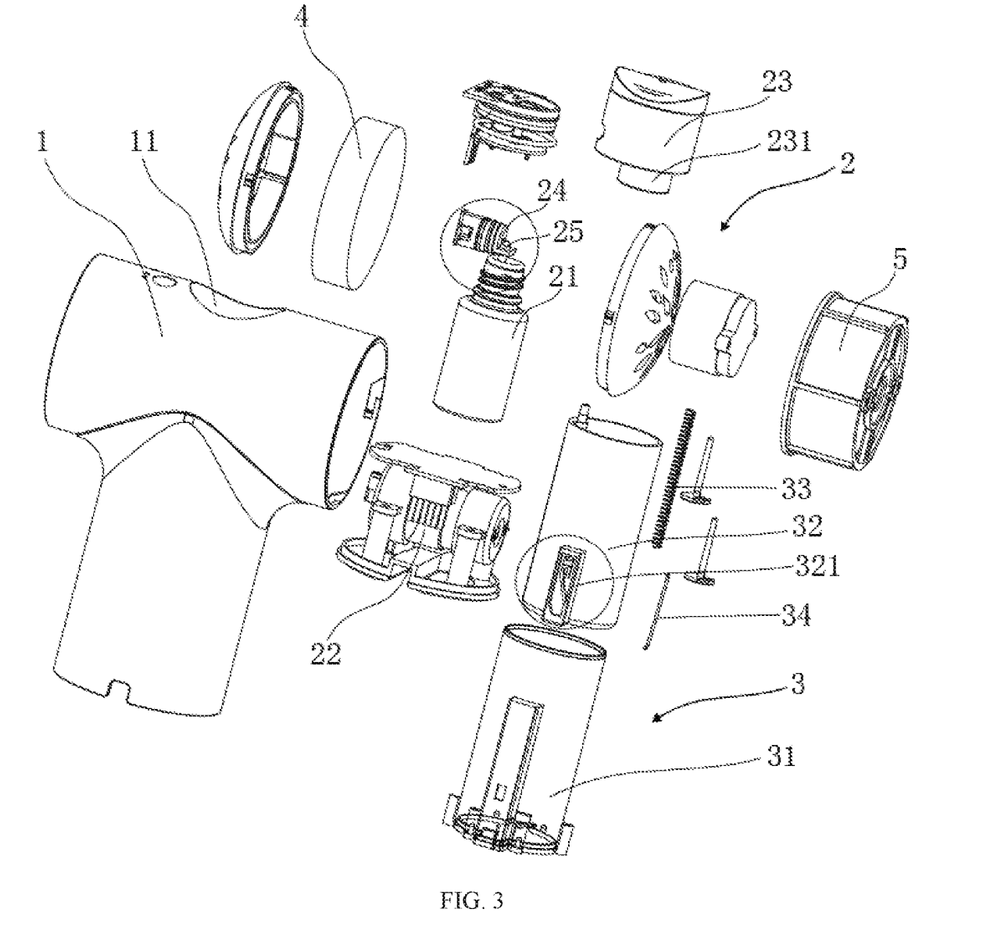
FIG. 3 is a schematic view of an explosion structure of FIG. 1.
Figure 7:
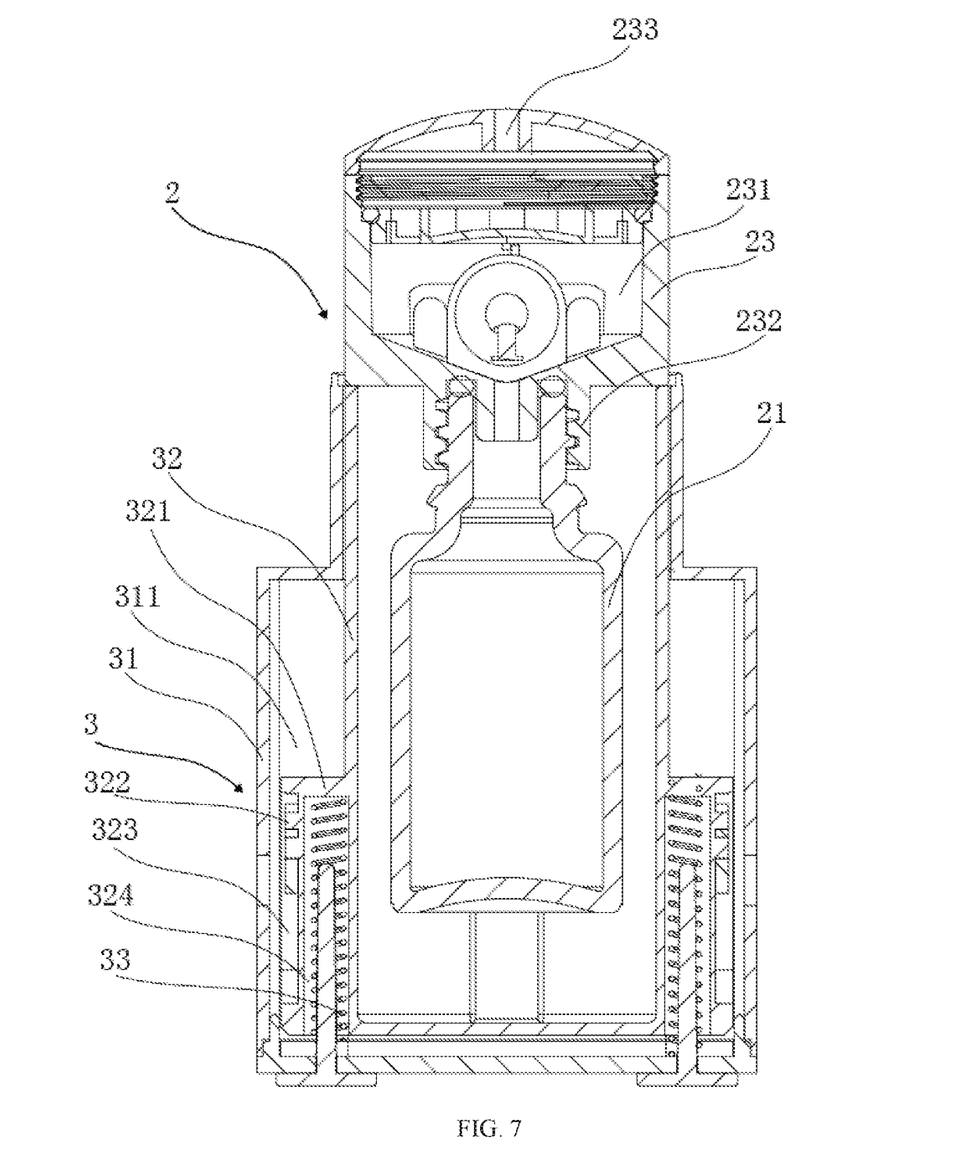
FIG. 7 is a schematic view of a section structure of FIG. 6.

In an embodiment, please refer to FIG. 2, FIG. 3, and FIG. 7. As a specific implementation of the aromatherapy device provided in the present application, the pop-up mechanism 3 includes an outer sleeve 31 fixed in the receiving chamber 11, an inner sleeve 32 configured for receiving the atomizing device 2, a spring 33 configured to elastically push the inner sleeve 32, outwardly and a locking structure 34 configured to lock the inner sleeve 32 into the outer sleeve 31. The inner sleeve 32 is slidably mounted in the outer sleeve 31, the spring 33 is placed in the outer sleeve 31, the locking structure 34 is connected with the outer sleeve 31, and the inner sleeve 32 is connected with the atomizing device 2.

In the embodiment, the pop-up mechanism 3 includes the outer sleeve 31, the inner sleeve 32, the spring 33, and the locking structure 34. The outer sleeve 31 is fixedly connected to the receiving chamber 11. The inner sleeve 32 is slidably installed in the outer sleeve 31. The spring 33 is placed in the outer sleeve 31, the inner sleeve 32 is elastically pushed from a bottom of the outer sleeve 31 to a top of the outer sleeve 31 by the spring, thereby when the atomizing device 2 is received in the receiving chamber 11, the atomizing device 2 is received and connected in the inner sleeve 32, then pressing the atomizing device 2 along the inner sleeve 32 (downward) to overcome the elastic pushing force of the spring 33 (upward), the atomizing device 2 slides along the outer sleeve 31 axially with the inner sleeve 32 to the inside of the outer sleeve 31, the inner sleeve 32 is locked in the outer sleeve 31 with a locking structure 34, so that the atomizing device 2 is built in and hidden in the housing 1 for using. In addition, by hiding the atomizing device 2 in the housing 1, the atomizing device 2 can be protected by the housing 1 to avoid damage to the atomizing device 2. At the same time, the atomizing device 2 is built into the housing 1 to reduce the volume of the entire aromatherapy device, so that the aromatherapy device can be placed in a small area. When the atomizing device 2 needs to be repaired or replaced, as long as the locking structure 34 unlocks the inner sleeve 32, and with the elastic pushing by the spring 33 (upward), the inner sleeve 32 is pushed from the bottom of the outer sleeve 31 to the top of the outer sleeve 31 by the spring 33, such that the atomizing device 2 slides along the outer sleeve 31 axially with the inner sleeve 32 to the outside of the outer sleeve 31, and then being ejected from the receiving chamber 11, the atomizing device 2 can be easily removed from the receiving chamber 11, and the atomizing device 2 can be easily repaired and replaced.

In another embodiment, as a specific implementation of the aromatherapy device provided in the present application, the pop-up mechanism 3 may further include an outer sleeve 31 fixed in a receiving chamber 11, an inner sleeve 32 configured to receive the atomizing device 2 and fittingly connect with the atomizing device 2, a spring 33 configured to elastically push the inner sleeve 32, outwardly and a locking structure 34 configured to lock the inner sleeve 32 into the outer sleeve 31. The inner sleeve 32 is slidably installed in the outer sleeve 31. The locking structure 34 is a buckle provided on the outer sleeve 31. The inner sleeve 32 is provided with a notch that cooperates with the buckle. The inner sleeve 32 is locked in the outer sleeve 31 by an interference fit buckle structure, which is convenient for the atomizing device 2 being built into the housing 1 to use, or for the atomizing device 2 being taken out from the receiving chamber 11 for easily repairing and replacing of the atomizing device 2. In addition, it is also possible to provide external threads on an outer wall of inner sleeve 32, and internal threads on an inner wall of outer sleeve 31, such that the inner sleeve 32 is locked in the outer sleeve 31 with the thread fit of the internal threads and the external threads to connect the inner sleeve 32, which is convenient for the atomizing device 2 being built into the housing 1 to use, or for the atomizing device 2 being taken out from the receiving chamber 11 for easily repairing and replacing of the atomizing device 2.

Figure 8:
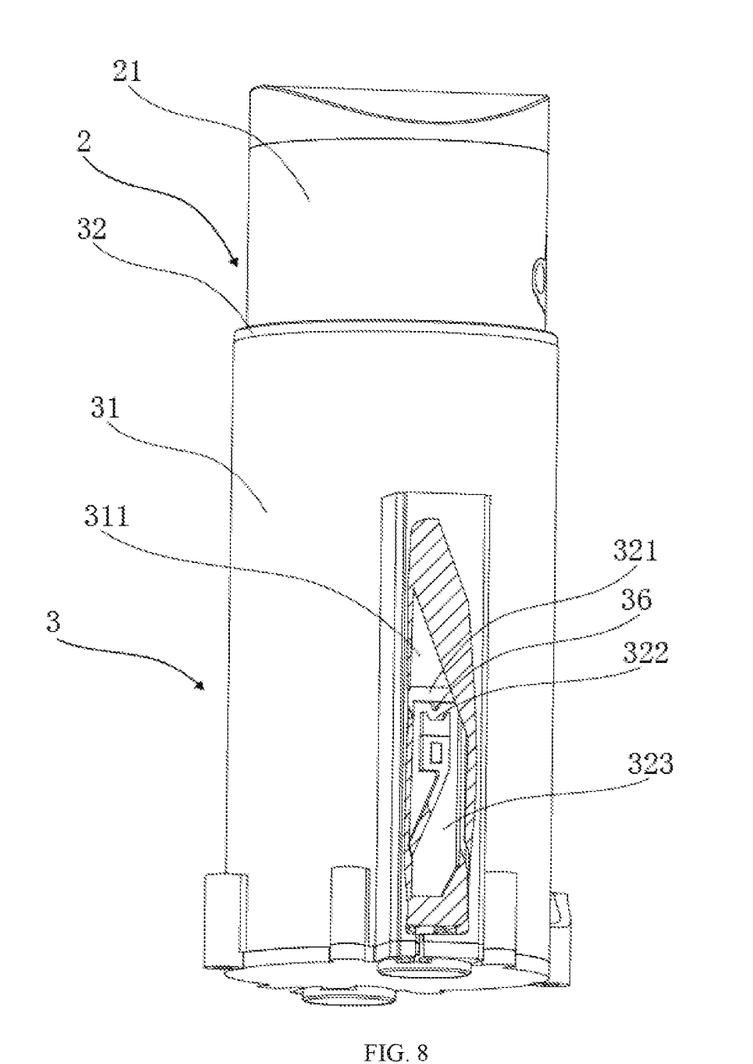
FIG. 8 is a schematic view of a partial section structure of FIG. 6.

In an embodiment, please refer to FIG. 7 and FIG. 8. As a specific implementation of the aromatherapy device provided in the present application, a sliding groove 311 is recessed on an inner sidewall of the outer sleeve 31, and an outer sidewall of the inner sleeve 32 is protruded with a sliding block 321 configured to be matched with the sliding groove 311.

Figure 9:
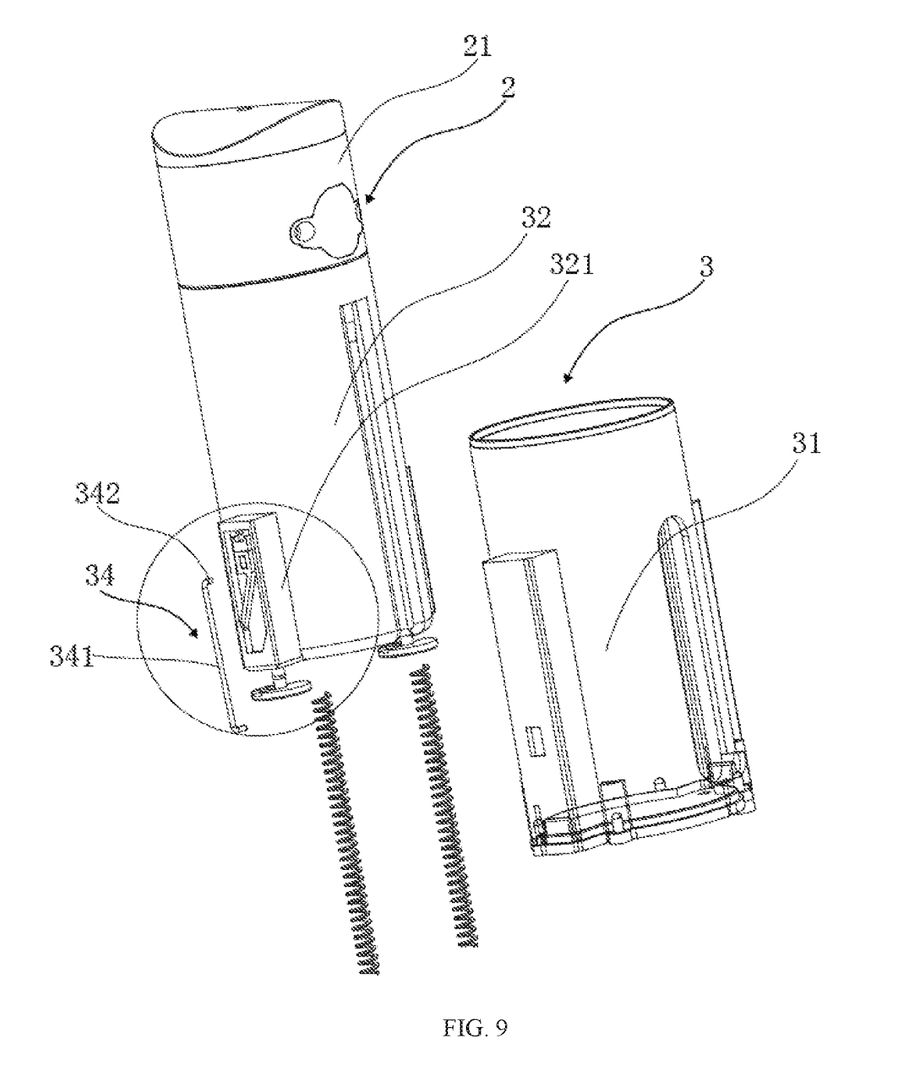
FIG. 9 is a partial enlarged structure view of FIG. 6.
Figure 10:
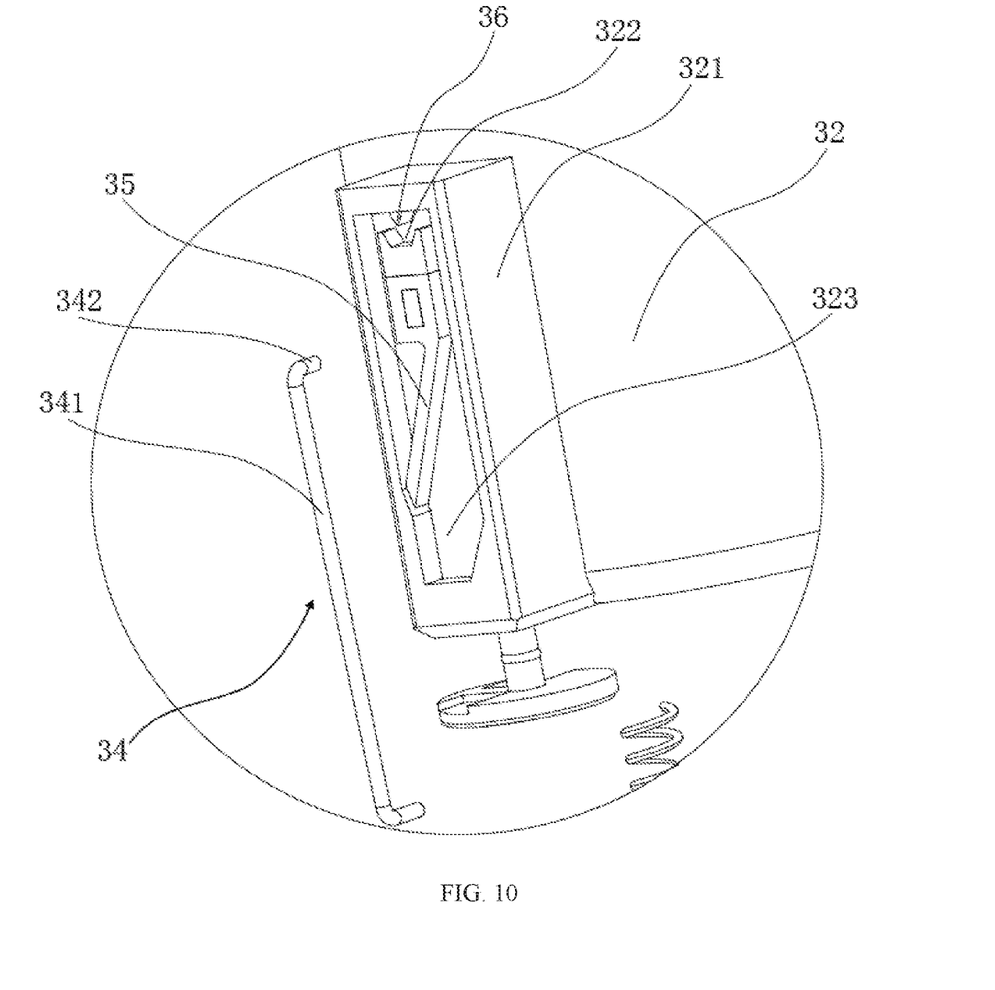
FIG. 10 is a partial enlarged structure view of FIG. 9.

In an embodiment, please refer to FIG. 3, FIG. 9, and FIG. 10. As a specific implementation of the aromatherapy device provided in the present application, the locking structure 34 includes a pull rod 341 disposed in the sliding groove 311 and a hook 342 bending from an end of the pull rod 341 toward the sliding block 321, the other end of the pull rod 341 is fixed at the outer sleeve 31, and the sliding block 321 is provided with a locking groove 322 configured for the hook 342 to be locked when placed in or unlocked when separated.

In the embodiment, the locking structure 34 includes a pull rod 341 and a hook 342 bent from one end of the pull rod 341 toward the sliding block 321. The hook is located in the sliding groove 311, and the end of the pull rod 341 away from the hook 342 is fixed to the outer sleeve 31. When inner sleeve 32 slides to the bottom of outer sleeve 31, the hook 342 is locked by the locking groove 322 to lock the inner sleeve 32 in the outer sleeve 31. The atomizing device 2 slides axially with the inner sleeve 32 along the outer sleeve 31 moving to the inside of outer sleeve 31, such that the atomizing device 2 is built in and hidden in housing 1 for using. When the atomizing device 2 needs to be repaired or replaced, as long as the hook 342 is disengaged from the locking groove 322 such that the inner sleeve 32 is unlocked, thereby with the elastic pushing of the spring 33 (upward), the inner sleeve 32 is pushed from the bottom of outer sleeve 31 toward the top of outer sleeve 31 by the spring 33, such that the atomizing device 2 slides with the inner sleeve 32 along the outer sleeve 31 axially to the outside of the outer sleeve 31, and then being ejected from the receiving chamber 11, the atomizing device can be easily took out from the receiving chamber 112, and for easy repairing and replacing of the atomizing device 2.

Figure 4:
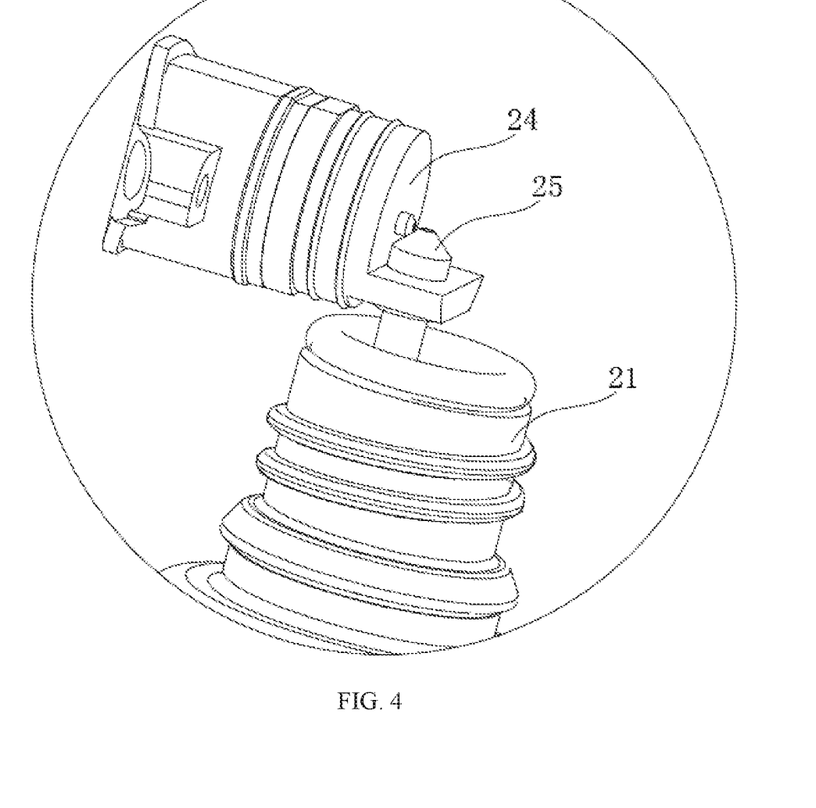
FIG. 4 is a partial enlarged structure view of FIG. 3.
Figure 5:
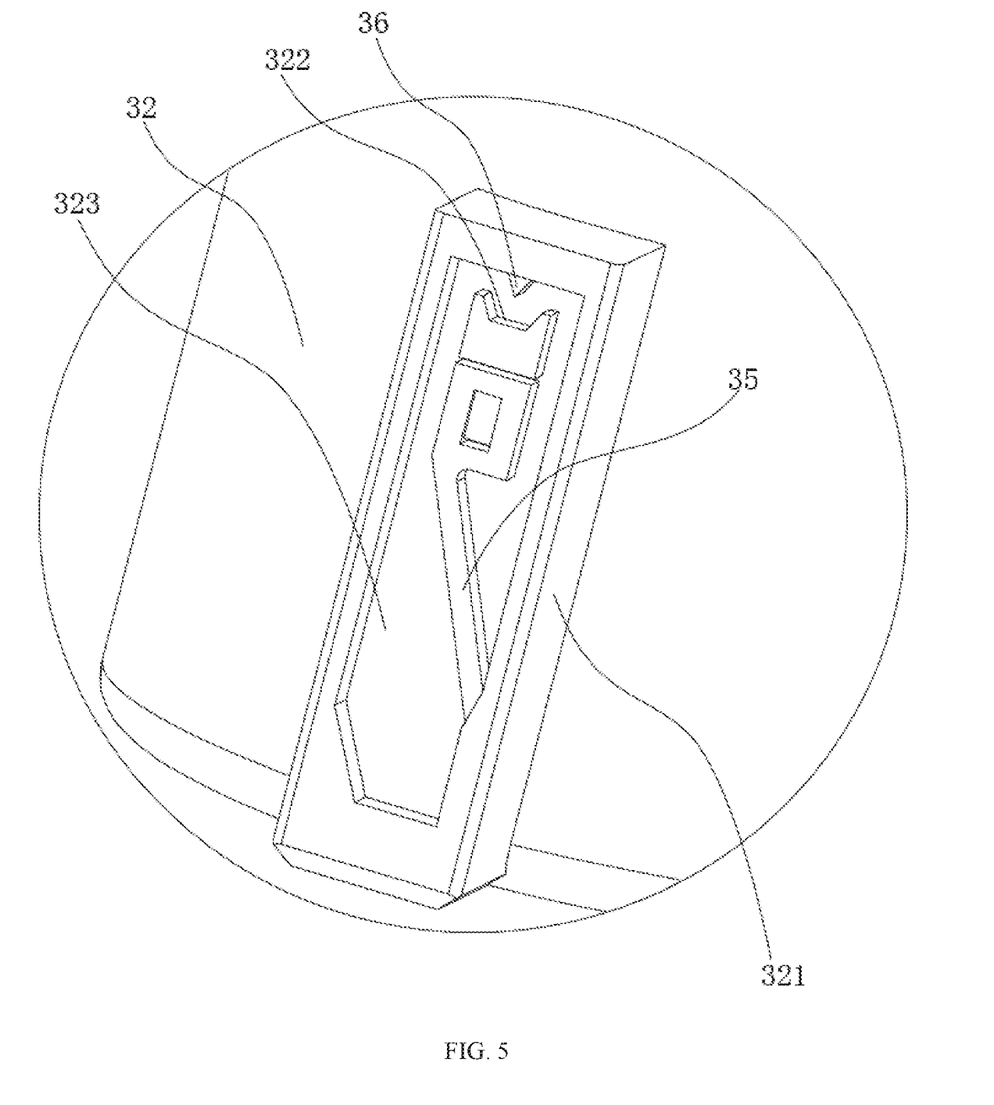
FIG. 5 is a partial enlarged structure view of FIG. 3.
Figure 6:
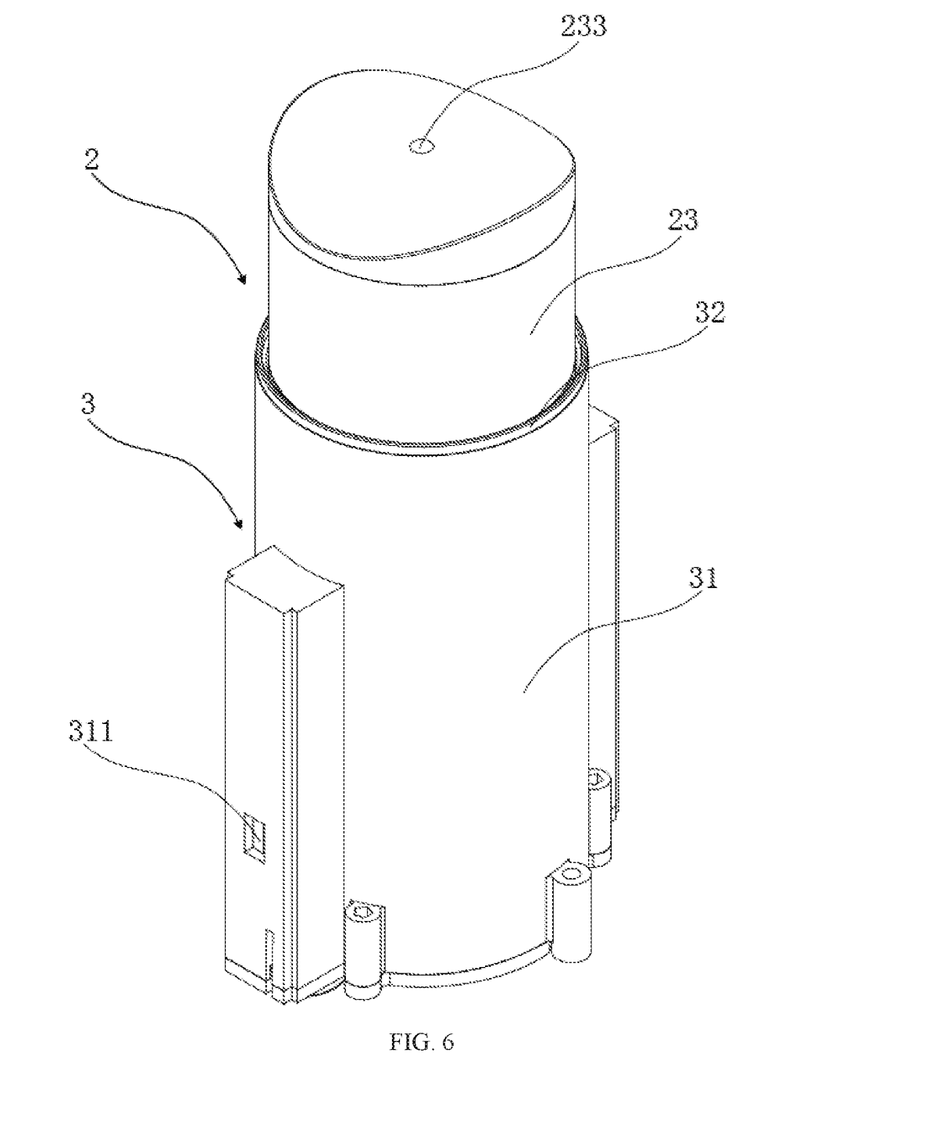
FIG. 6 is a schematic view of a perspective structure of an pop-up mechanism provided by an embodiment of the present application.

In an embodiment, please refer to FIG. 4, FIG. 8, and FIG. 10. As a specific implementation of the aromatherapy device provided in the present application, the sliding block 321 is provided with a limiting groove 323 configured for guiding the hook 342 to be moved into the locking groove 322 or separated from the locking groove 322, and the locking groove 322 is located in the limiting groove 323.

In the embodiment, the sliding groove 321 is provided with a limiting groove 323 that guides the hook 342 to be placed into the locking groove 322 or to be separated from the locking groove 322, and the locking groove 322 is located in the limiting groove, thereby the limiting groove 323 is configured to guide the moving path of the hook 342, such that the hook 342 can be smoothly placed into the locking groove 322 or to be separated from the locking groove 322, to realize the locking or unlocking of the inner sleeve 32, the smoothness and stability of the hook 342 being placed into the locking groove 322 or separated from the locking groove 322 is enhanced, and it is convenient for the installation and removal of the atomizing device 2.

In an embodiment, please refer to FIG. 4, FIG. 8, and FIG. 10. As a specific implementation of the aromatherapy device provided in the present application, the limiting groove 323 is provided with a limiting elastic arm 35 configured to fittingly stop the hook 342 to limit the moving path of the hook 342 in the limiting groove 323.

In the embodiment, the limiting elastic arm 35 is provided in the limiting groove 323, and the limiting elastic arm 35 is fittingly stopping the hook 342 to limit the moving path of the hook 342 in the limiting groove 323, thereby further enabling the hook 342 to be quickly and smoothly placed or separated from the locking groove 322 to achieve locking or unlocking of inner sleeve 32, the smoothness and stability of the hook 342 being placed into the locking groove 322 or separated from the locking groove 322 is enhanced, and it is convenient for the installation and removal of the atomizing device 2.

In an embodiment, please refer to FIG. 4, FIG. 8, and FIG. 10. As a specific implementation of the aromatherapy device provided in the present application, an inner sidewall of the limiting groove 323 is protruded with a limiting block 36 configured for sopping the hook 342 to limit the moving path of the hook 342, the position of the limiting block 36 is arranged corresponding to the position of an opening of the locking groove 322.

In the embodiment, the limiting block 36 is protruded on the inner sidewall of the limiting groove 323, when the hook 342 is separated from the locking groove 322, the limiting block is fittingly stopping the hook 342 to limit the moving path of the hook 342, thereby the hook 342 can be quickly and stably separated from the locking groove 322, the fast unlocking of the inner sleeve 32 can be achieved, which can improve the efficiency of installation and removal of the atomizing device 2, and enhance the stability of the installation and removal of the atomizing device 2.

In one embodiment, please refer to FIG. 7. As a specific implementation of the aromatherapy device provided in the present application, the sliding block 321 is provided with a hole 324 for a top end of the spring 33 being placed into, and the hole 324 is disposed along the axial direction of the inner sleeve 32, and a bottom end of the spring 33 is connected to the inner bottom surface of the outer sleeve 31.

In the embodiment, the sliding block 321 is provided with a hole 324 for the top end of the spring 33 being placed into, and the hole 324 is extended along the axial direction of the inner sleeve 32. The top end of the spring 33 is placed in the hole 324, and the bottom end of the spring 33 is connected to the inner bottom surface of the outer sleeve 31, such that the spring 33 is limited by the hole 324, and the stability of the spring ejection inner sleeve 32 is enhanced.

In an embodiment, please refer to FIG. 2, FIG. 3, and FIG. 4. As a specific implementation of the aromatherapy device provided in the present application, the atomizing device 2 includes an essential oil bottle 21 configured to store essential oils, an air pump 22 configured to provide air flow, an atomizing cover 23 provided with an atomizing cavity 231, an air spraying nozzle 24 placed in the atomizing cavity 231, an air pipe (not shown in the figure) configured for connecting the air pump 22 and the air spraying nozzle 24 an oil suction pipe (not shown in the figure) extending into of the essential oil bottle, and an oil spraying nozzle 25 connected with the oil suction pipe.

The atomizing cover 23 is provided with a connecting port 232 configured for fittingly connecting the essential oil bottle 21, the connecting port 232 is in communication with the atomizing cavity 231, a position of an air outlet of the air spraying nozzle 24 is located at a position corresponding to an oil outlet of the oil spraying nozzle, the atomizing cover 23 is provided with a mist outlet 233 in communication with the atomizing cavity 231, and the atomizing cavity 231 is in communication with the mist outlet 233.

In the embodiment, the atomizing cover 23 is provided with an atomizing cavity 231, and the atomizing cover 23 is provided with a mist outlet 233 that communicates with the atomizing cavity 231, the lower end of the atomizing cover 23 is provided with a connecting port 232, the bottle mouth of the essential oil bottle 21 is connected to the atomizing cover 23 through the connecting port 232. The atomizing cover 23 is installed on housing 1, and the air pump 22 is installed in the housing 1, the air pump 22 is supported and protected by housing 1. One end of the air pipe is connected to the air pump 22, and the other end of the air pipe is connected to the air spraying nozzle 24. The air flow provided by the air pump 22 is transmitted to the air spraying nozzle 24 through the air pipe, and is sprayed from the air spraying nozzle 24. The oil outlet of the oil spraying nozzle 25 is located in the atomizing cavity 231, the air outlet of the air spraying nozzle 24 is located at the corresponding position of the oil spraying nozzle 25, and the oil spraying nozzle 25 is located at the corresponding position of the connecting port 232, such that the oil spraying nozzle 25 can extract essential oil from essential oil bottle 21 through the oil suction pipe, when the connecting port is in communication with the essential oil bottle 21, and the upper end of oil spraying nozzle 25 extends into atomizing cavity 231, and the outlet of air spraying nozzle 24 is located at oil spraying nozzle 25. Therefore, when the air pump 22 generates high-pressure gas and sprays it from the air spraying nozzle 24, a negative pressure is formed at the nozzle of the upper end of the oil spraying nozzle 25, so as to extract essential oil from the essential oil bottle 21 through the oil suction pipe at the negative pressure, and the extracted essential oil is sprayed from the oil spraying port of the oil spraying nozzle 25. The sprayed liquid droplets will be scattered by the high-speed airflow sprayed from the air spraying nozzle 24 to be atomized to form a mixed airflow, and the pressure in the atomizing cavity 231 is increased at the same time. Since the connecting port 232 is connected to essential oil bottle 21, then the airflow in the atomizing cavity 231 is sprayed from the mist outlet 233, so as to realize the aroma of the air in the car and achieve the purpose of improving the air quality in the car.

In an embodiment, please refer to FIG. 2, FIG. 4, and FIG. 7. As a specific implementation of the aromatherapy device provided in the present application, external threads are provided on the outer sidewall of the bottle mouth of essential oil bottle 21, the inner sidewall of the connecting port 232 is provided with internal threads cooperated with the external threads.

In the embodiment, external threads are provided on the outer sidewall of the bottle mouth of essential oil bottle 21, and internal threads are provided on the inner sidewall of connecting port 232, by matching the external threads with the internal threads, it is convenient and fast to connect the essential oil bottle 21 to the connecting port 232 and can enhance the tightness of the joint between the essential oil bottle 21 and the connecting port 232.

In an embodiment, please refer to FIG. 2 and FIG. 4. As a specific implementation of the aromatherapy device provided in the present application, the bottom of the atomizing cavity 231 has an inclined surface extending obliquely to the connecting port 232.

In the embodiment, the bottom of the atomizing cavity 231 has an inclined surface that extends obliquely to the connecting port 232, by the guidance of the inclined surface, large particles of essential oil droplets are guided back to the essential oil bottle 21 to avoid affecting the effect of atomizing the essential oil and reducing the waste of the essential oil.

In an embodiment, please refer to FIG. 3 and FIG. 4. As a specific implementation of the aromatherapy device provided in the present application, an end of the oil spraying nozzle 25 away from the oil outlet is provided with a connection sleeve, and the connection sleeve can be detachably connected with a oil suction pipe, which is placed in essential oil bottle 21.

In the embodiment, the a connection sleeve is provided at the end of the oil spraying nozzle 25 away from the oil outlet, and the oil suction pipe is detachably connected to the connection sleeve, and oil suction pipe is connected to the lower end of the oil spraying nozzle 25, and the essential oil in essential oil bottle 21 is pumped to oil spraying nozzle 25 by the oil suction pipe under the effect of negative pressure. In addition, the oil suction pipe is detachably connected to the connection sleeve of the oil spraying nozzle 25, and oil suction pipes of different lengths can be replaced according to different essential oil bottle 21 to improve the adaptability.

In an embodiment, please refer to FIG. 3 and FIG. 4. As a specific implementation of the aromatherapy device provided in the present application, the housing is provided therein with a receiving bin configured to receive and position the essential oil bottle 21, so as to receive and position the essential oil bottle 21 in the receiving bin, which facilitates the installation of essential oil bottle 21 and enhances the stability of installation of essential oil bottle 21.

In an embodiment, please refer to FIG. 3 and FIG. 4. As a specific implementation of the aromatherapy device provided in the present application, an axis direction of the outlet of the is directed to the top of the upper sidewall of the oil spraying nozzle 25, such that when the air is sprayed from the outlet of the air spraying nozzle 24, the air can cover the upper end of the oil spraying nozzle 25 to better form a vacuum at the upper end of the oil spraying nozzle 25. At the same time, the top of the upper sidewall of the oil spraying nozzle 25 can change the flow direction of the airflow air sprayed from the air spraying nozzle 24, which can better atomize the essential oil droplets extracted by the oil spraying nozzle 25.

In one embodiment, please refer to FIG. 3 and FIG. 4. As a specific implementation of the aromatherapy device provided in the present application, an axial direction of the outlet of the air spraying nozzle 24 is in inclined upwards directed to the top of the upper sidewall of the oil spraying nozzle 25. This structure can prevent the air sprayed by the air spraying nozzle 24 from blowing into the nozzle at the upper end of the oil spraying nozzle 25, such that the essential oil can be better extracted, and the extracted essential oil can be obliquely and upwardly blown, so that the essential oil can be better atomized.

In an embodiment, please refer to FIG. 3 and FIG. 4. As a specific implementation of the aromatherapy device provided in the present application, the side wall of the upper end of the oil spraying nozzle 25 is conical, such that the sidewall of the upper end of the oil spraying nozzle can guide the airflow sprayed by the air spraying nozzle 24 upward, so that the airflow can better atomize the essential oil extracted by the oil spraying nozzle 25. In some other embodiments, the sidewall of the upper end of the oil spraying nozzle 25 may also have a circular arc shape protruding upward.

In an embodiment, please refer to FIG. 2, FIG. 3, and FIG. 4. As a specific implementation of the aromatherapy device provided in the present application, the housing 1 is provided with an air purification cavity 12. The aromatherapy device further includes fan 5 and a filter net 4 configured for filtering and purifying the air, the filter net 4 is placed in the air purification cavity 12, the housing is provided with an air inlet 13 and an air outlet 14 respectively in communication with the air purification cavity 12, and the filter net 4 is disposed at the air inlet.

In the embodiment, the fan 5 and filter net 4 are set in housing 1, and the fan 5 generates negative pressure airflow in housing 1 and the air in the vehicle is sucked into housing 1 from air inlet 13 of housing 1 and passes through air inlet 13 to be filtered and purified by the filter net 4, and the filtered and purified air is discharged into the vehicle from the air outlet 14 of housing 1 to realize the circulation purification function of the air in the vehicle. In this way, the air in the vehicle can be scented and purified, and the air quality in the vehicle environment can be improved.

The aforementioned embodiments are only preferred embodiments of the present application. For one of ordinary skill in the art, according to the thought of the present application, specific implementation modes and application scopes may be modified, and the content of the specification should not be interpreted as any limitation to the present application.

What is claimed is:

1. An aromatherapy device, comprising:
a housing; and
an atomizing device, configured for atomizing essential oil to be sprayed out;
wherein the housing is provided with a receiving chamber configured for fittingly receiving the atomizing device, and the receiving chamber is provided therein with a pop-up mechanism configured for launching the atomizing device out;
wherein the pop-up mechanism comprises:
an outer sleeve, fixed in the receiving chamber;
an inner sleeve, configured for receiving the atomizing device;
a spring, configured to elastically push the inner sleeve, outwardly; and
a locking structure, configured to lock the inner sleeve into the outer sleeve;
the inner sleeve is slidably mounted in the outer sleeve, the spring is placed in the outer sleeve, the locking structure is connected with the outer sleeve, and the inner sleeve is connected with the atomizing device.

2. The aromatherapy device of claim 1, wherein an inner sidewall of the outer sleeve is concaved to form a sliding groove, and an outer sidewall of the inner sleeve is protruded with a sliding block configured to be matched with the sliding groove.

3. The aromatherapy device of claim 2, wherein the locking structure comprises a pull rod disposed in the sliding groove and a hook bending from an end of the pull rod toward the sliding block, the other end of the pull rod is fixed at the outer sleeve, and the sliding block is provided with a locking groove configured for enabling the hook to be locked when placed in or unlocked when separated.

4. The aromatherapy device of claim 3, wherein the sliding block is provided with a limiting groove configured for guiding the hook to be moved into the locking groove or separated from the locking groove, and the locking groove is located in the limiting groove.

5. The aromatherapy device of claim 4, wherein the limiting groove is provided with a limiting elastic arm configured for fittingly stopping the hook to limit a moving path of the hook in the limiting groove.

6. The aromatherapy device of claim 4, wherein an inner sidewall of the limiting groove is protruded with a limiting block configured for stopping the hook to limit a moving path of the hook, and a position of the limiting block is corresponding to an opening position of the locking groove.

7. The aromatherapy device of claim 2, wherein the sliding block is provided with a hole configured for a top end of the spring to be placed into, and the hole extends along an axis direction of the inner sleeve, and a bottom end of the spring is connected with an inner bottom surface of the outer sleeve.

8. The aromatherapy device of claim 1, wherein the atomizing device comprises:
   an essential oil bottle, configured to store essential oils;
   an air pump, configured to provide air flow;
   an atomizing cover, provided with an atomizing cavity;
   an air spraying nozzle, placed in the atomizing cavity;
   an air pipe, configured for connecting the air pump and the air spraying nozzle;
   an oil suction pipe, extending into of the essential oil bottle; and
   an oil spraying nozzle, connected with the oil suction pipe;
   the atomizing cover is provided with a connecting port configured for fittingly connecting the essential oil bottle, the connecting port is in communication with the atomizing cavity, a position of an air outlet of the air spraying nozzle is located at a position corresponding to an oil outlet of the oil spraying nozzle, the atomizing cover is provided with a mist outlet in communication with the atomizing cavity, and the atomizing cavity is in communication with the mist outlet.

9. The aromatherapy device of claim 1, wherein the housing is provided with an air purification chamber, the aromatherapy device further comprises a fan and a filter net configured to filter and purify the air, the filter net is placed in the air purification chamber, the housing is provided thereon with an air inlet and an air outlet respectively in communication with the air purification chamber, and the filter net is disposed at the air inlet.

10. The aromatherapy device of claim 2, wherein the atomizing device comprises:
    an essential oil bottle, configured to store essential oils;
    an air pump, configured to provide air flow;
    an atomizing cover, provided with an atomizing cavity;
    an air spraying nozzle, placed in the atomizing cavity;
    an air pipe, configured for connecting the air pump and the air spraying nozzle;
    an oil suction pipe, extending into of the essential oil bottle; and
    an oil spraying nozzle, connected with the oil suction pipe;
    the atomizing cover is provided with a connecting port configured for fittingly connecting the essential oil bottle, the connecting port is in communication with the atomizing cavity, a position of an air outlet of the air spraying nozzle is located at a position corresponding to an oil outlet of the oil spraying nozzle, the atomizing cover is provided with a mist outlet in communication with the atomizing cavity, and the atomizing cavity is in communication with the mist outlet.

11. The aromatherapy device of claim 3, wherein the atomizing device comprises:
    an essential oil bottle, configured to store essential oils;
    an air pump, configured to provide air flow;
    an atomizing cover, provided with an atomizing cavity;
    an air spraying nozzle, placed in the atomizing cavity;
    an air pipe, configured for connecting the air pump and the air spraying nozzle;
    an oil suction pipe, extending into of the essential oil bottle; and
    an oil spraying nozzle, connected with the oil suction pipe;
    the atomizing cover is provided with a connecting port configured for fittingly connecting the essential oil bottle, the connecting port is in communication with the atomizing cavity, a position of an air outlet of the air spraying nozzle is located at a position corresponding to an oil outlet of the oil spraying nozzle, the atomizing cover is provided with a mist outlet in communication with the atomizing cavity, and the atomizing cavity is in communication with the mist outlet.

12. The aromatherapy device of claim 4, wherein the atomizing device comprises:
    an essential oil bottle, configured to store essential oils;
    an air pump, configured to provide air flow;
    an atomizing cover, provided with an atomizing cavity;
    an air spraying nozzle, placed in the atomizing cavity;
    an air pipe, configured for connecting the air pump and the air spraying nozzle;
    an oil suction pipe, extending into of the essential oil bottle; and
    an oil spraying nozzle, connected with the oil suction pipe;
    the atomizing cover is provided with a connecting port configured for fittingly connecting the essential oil bottle, the connecting port is in communication with the atomizing cavity, a position of an air outlet of the air spraying nozzle is located at a position corresponding to an oil outlet of the oil spraying nozzle, the atomizing cover is provided with a mist outlet in communication with the atomizing cavity, and the atomizing cavity is in communication with the mist outlet.

13. The aromatherapy device of claim 5, wherein the atomizing device comprises:
    an essential oil bottle, configured to store essential oils;
    an air pump, configured to provide air flow;
    an atomizing cover, provided with an atomizing cavity;
    an air spraying nozzle, placed in the atomizing cavity;
    an air pipe, configured for connecting the air pump and the air spraying nozzle;
    an oil suction pipe, extending into of the essential oil bottle; and
    an oil spraying nozzle, connected with the oil suction pipe;
    the atomizing cover is provided with a connecting port configured for fittingly connecting the essential oil bottle, the connecting port is in communication with the atomizing cavity, a position of an air outlet of the air spraying nozzle is located at a position corresponding to an oil outlet of the oil spraying nozzle, the atomizing cover is provided with a mist outlet in communication with the atomizing cavity, and the atomizing cavity is in communication with the mist outlet.

14. The aromatherapy device of claim 6, wherein the atomizing device comprises:
    an essential oil bottle, configured to store essential oils;
    an air pump, configured to provide air flow;
    an atomizing cover, provided with an atomizing cavity;
    an air spraying nozzle, placed in the atomizing cavity;

an air pipe, configured for connecting the air pump and the air spraying nozzle;

an oil suction pipe, extending into of the essential oil bottle; and an oil spraying nozzle, connected with the oil suction pipe;

the atomizing cover is provided with a connecting port configured for fittingly connecting the essential oil bottle, the connecting port is in communication with the atomizing cavity, a position of an air outlet of the air spraying nozzle is located at a position corresponding to an oil outlet of the oil spraying nozzle, the atomizing cover is provided with a mist outlet in communication with the atomizing cavity, and the atomizing cavity is in communication with the mist outlet.

15. The aromatherapy device of claim 7, wherein the atomizing device comprises:

an essential oil bottle, configured to store essential oils;

an air pump, configured to provide air flow;

an atomizing cover, provided with an atomizing cavity;

an air spraying nozzle, placed in the atomizing cavity;

an air pipe, configured for connecting the air pump and the air spraying nozzle;

an oil suction pipe, extending into of the essential oil bottle; and an oil spraying nozzle, connected with the oil suction pipe;

the atomizing cover is provided with a connecting port configured for fittingly connecting the essential oil bottle, the connecting port is in communication with the atomizing cavity, a position of an air outlet of the air spraying nozzle is located at a position corresponding to an oil outlet of the oil spraying nozzle, the atomizing cover is provided with a mist outlet in communication with the atomizing cavity, and the atomizing cavity is in communication with the mist outlet.

16. The aromatherapy device of claim 2 wherein the housing is provided with an air purification chamber, the aromatherapy device further comprises a fan and a filter net configured to filter and purify the air, the filter net is placed in the air purification chamber, the housing is provided thereon with an air inlet and an air outlet respectively in communication with the air purification chamber, and the filter net is disposed at the air inlet.

17. The aromatherapy device of claim 3 wherein the housing is provided with an air purification chamber, the aromatherapy device further comprises a fan and a filter net configured to filter and purify the air, the filter net is placed in the air purification chamber, the housing is provided thereon with an air inlet and an air outlet respectively in communication with the air purification chamber, and the filter net is disposed at the air inlet.

* * * * *